United States Patent [19]
Katsilometes et al.

[11] Patent Number: 5,866,335
[45] Date of Patent: Feb. 2, 1999

[54] PREPARATION OF DERIVATIZED 10,10'-SUBSTITUTED-9,9'-BIACRIDINE LUMINESCENT MOLECULES AND SIGNAL SOLUTIONS

[75] Inventors: George W. Katsilometes, 3660 B Village Dr., Carlsbad, Calif. 92008; Pak T. Ho, San Mateo, Calif.

[73] Assignee: George W. Katsilometes, Lava Hot Springs, Id.

[21] Appl. No.: 767,288

[22] Filed: Dec. 16, 1996

Related U.S. Application Data

[63] Continuation of Ser. No. 265,481, Jun. 24, 1994, abandoned.

[51] Int. Cl.$^6$ .................................................. G01N 33/532
[52] U.S. Cl. ................................ 435/6; 435/7.1; 435/7.5; 435/9.73; 436/501; 436/518; 436/543; 436/544; 436/164; 436/172; 252/700; 530/300; 530/345; 530/391.3; 530/403; 530/802; 536/24.3; 536/25.32
[58] Field of Search .................................. 435/6, 7.1, 7.5, 435/973; 436/501, 518, 543, 544, 164, 172, 805, 807, 808; 252/700; 422/52; 530/300, 345, 391.3, 403, 802; 536/24.3, 25.32

[56] References Cited

U.S. PATENT DOCUMENTS

| | | | |
|---|---|---|---|
| 4,478,817 | 10/1984 | Campbell et al. | 435/7.1 |
| 5,340,714 | 8/1994 | Katsilometes | 435/6 |

FOREIGN PATENT DOCUMENTS

| | | |
|---|---|---|
| 0408463 | 1/1991 | European Pat. Off. . |
| 2233450 | 1/1991 | United Kingdom . |

OTHER PUBLICATIONS

Vlasenko et al., J. Biolum. Chemilum, vol. 4, pp. 164–176 (1989) "An Investigation on teh Catalytic Mechanism of Enhanced Chemiluminescence: Immunochemical Applications of this Reaction".

Papadopoulos et al., J. prakt. Chem., vol. 335, pp. 633–636 (1993) "Synthesis of N,N'–Dialkyl–9–9'–Buacridylidenes and 9,9'–Biacridinium Nitrates Containing Long Alkyl Chains".

Papadopoulos et al., Tetrahedron Letters, vol. 35, No. 8, pp. 1371–1372 (1993) "Synthesis of Novel Protected Hemianimal N–Methoxymethyl–N'–Methyl–9,9'–Biacridylidene from Lucigenin".

*Primary Examiner*—Lora M. Green
*Attorney, Agent, or Firm*—Karen S. Smith; Flehr Hohbach Test Albritton & Herbert LLP

[57] ABSTRACT

The synthesis of 10,10'-substituted-9,9'-biacridine molecules and their derivatives is disclosed. These molecules are shown to catalyze the production of light by chemiluminescence in the presence of a signal solution having at a pH from about 10.0 to about 14.0, at a concentration effective for producing a chemiluminescent signal, a chelating agent, a sulfoxide, a reducing sugar, an oxidant or combination of oxidants, an alcohol and aqueous sodium tetraborate. These 10,10'-substituted-9,9'-biacridines are used alone or attached to haptens or macromolecules and are utilized as labels in the preparation of chemiluminescent, homogeneous or heterogeneous assays. They are also used in conjunction with other chemiluminescent label molecules to produce multiple analyte chemiluminescent assays.

31 Claims, 4 Drawing Sheets

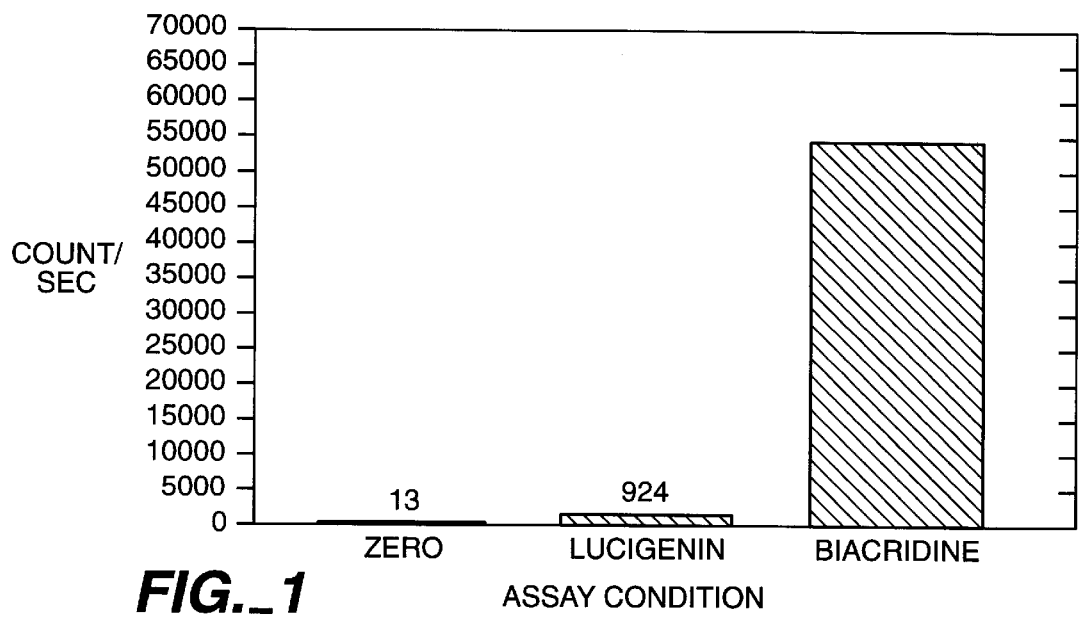
FIG._1
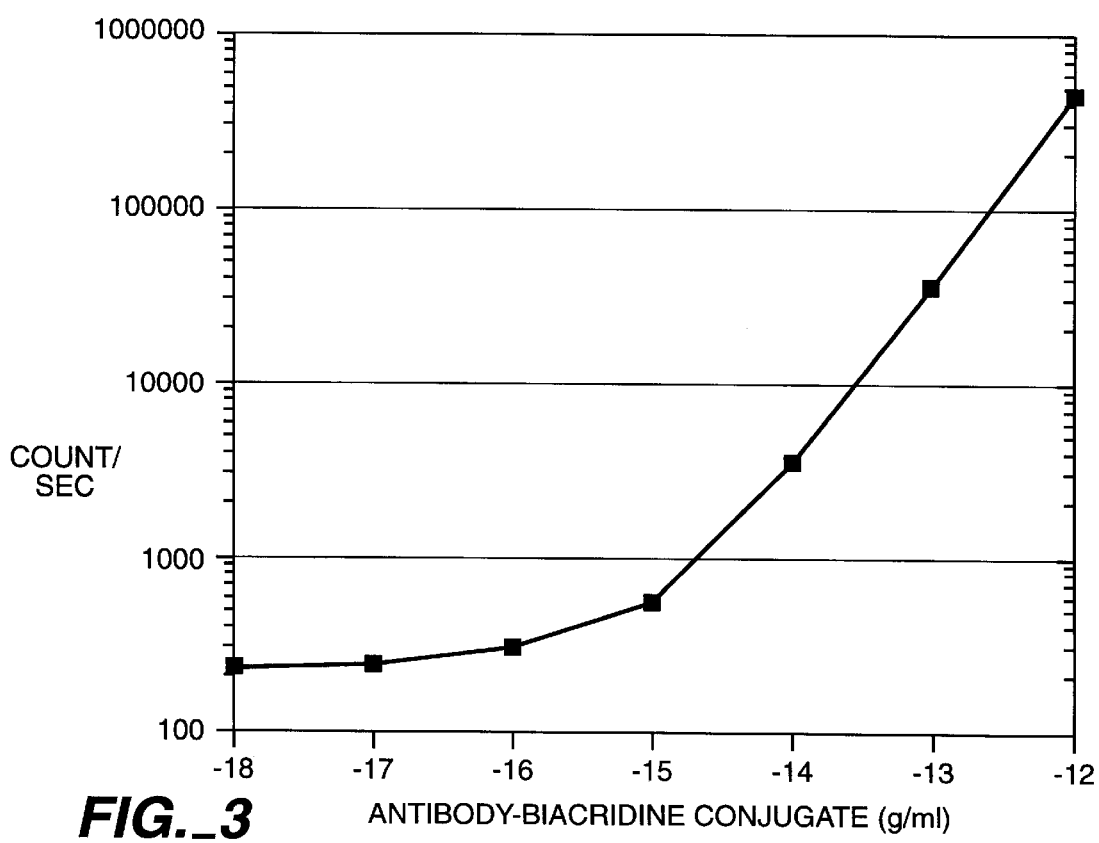
FIG._3

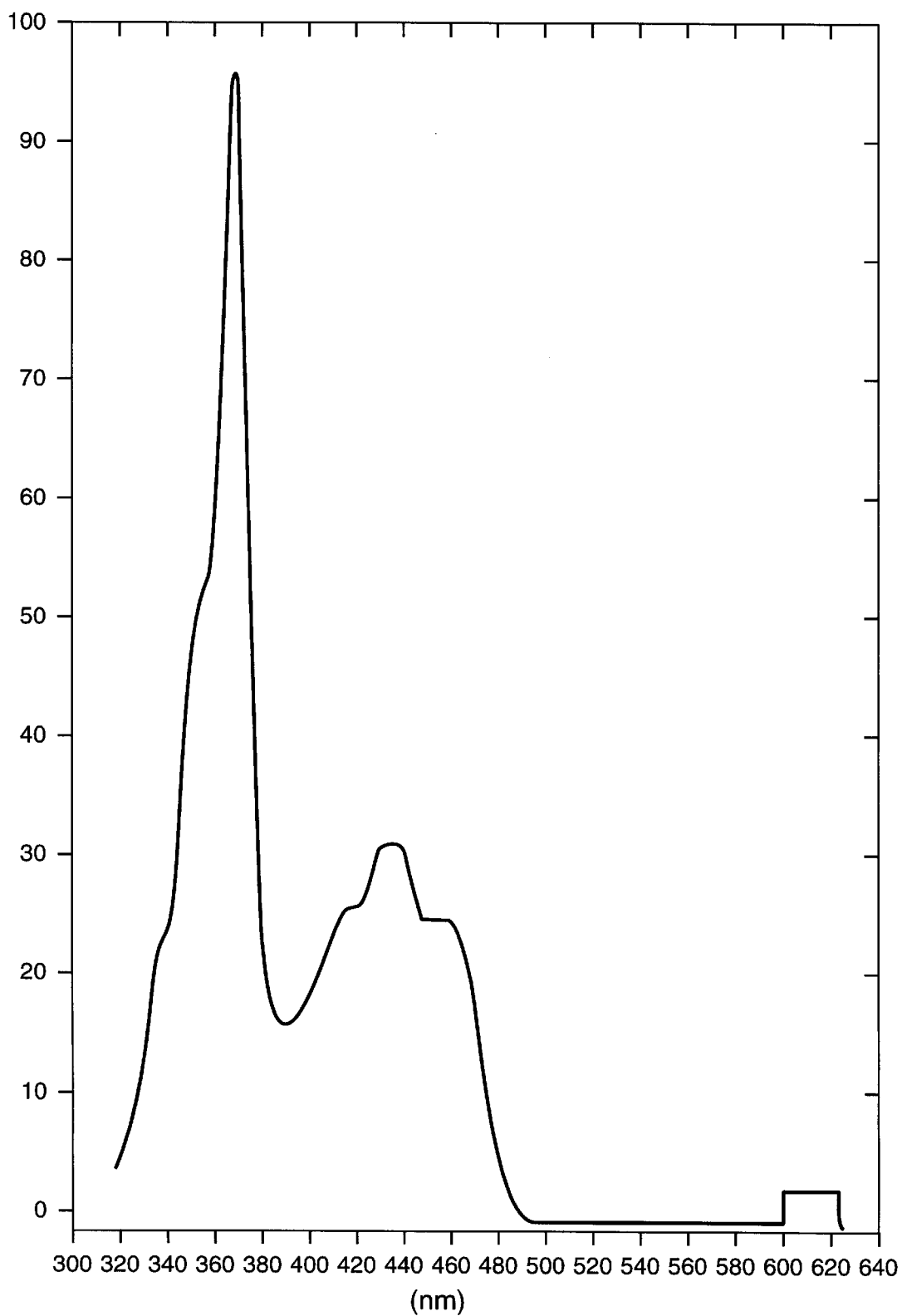
FIG._2

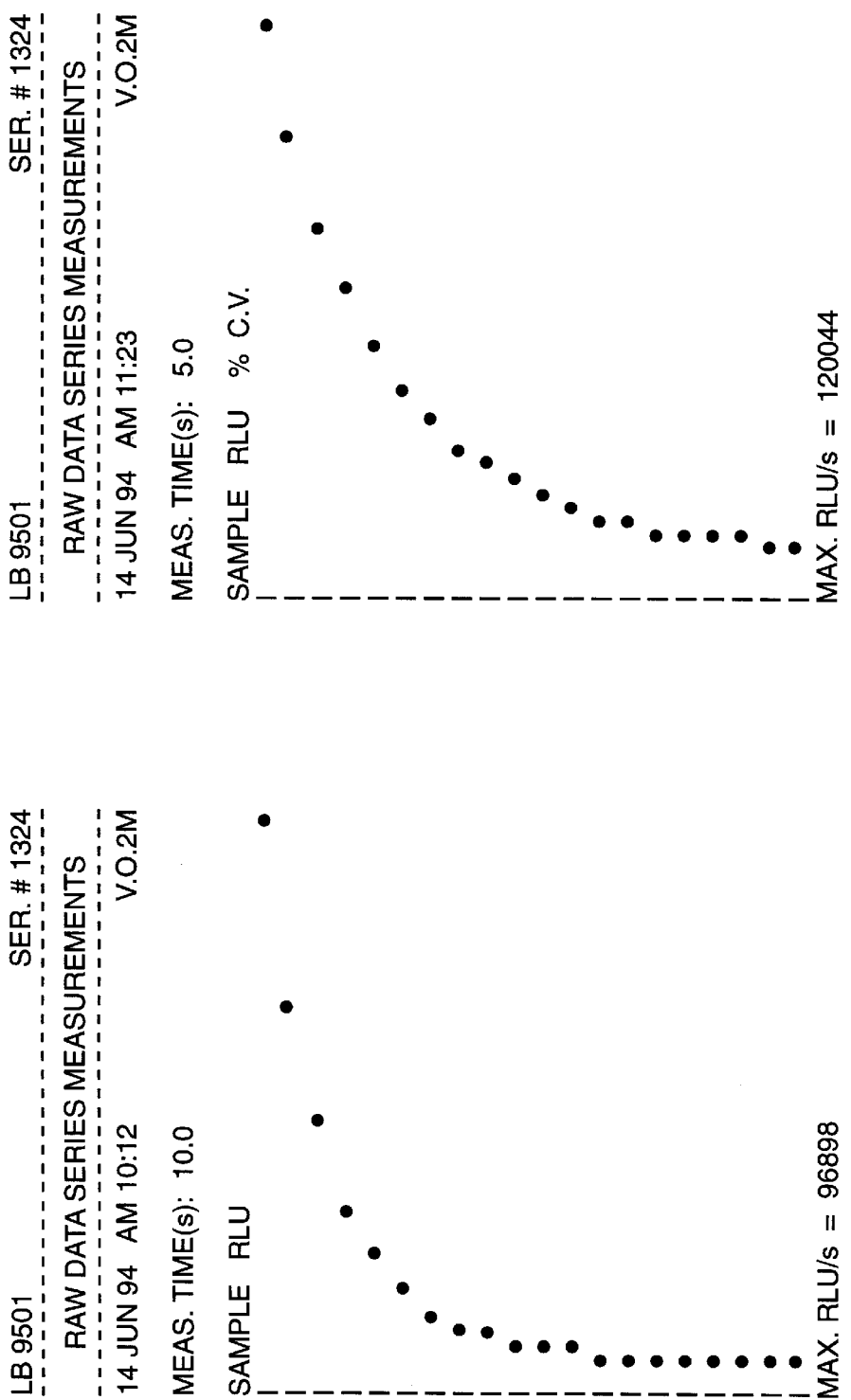

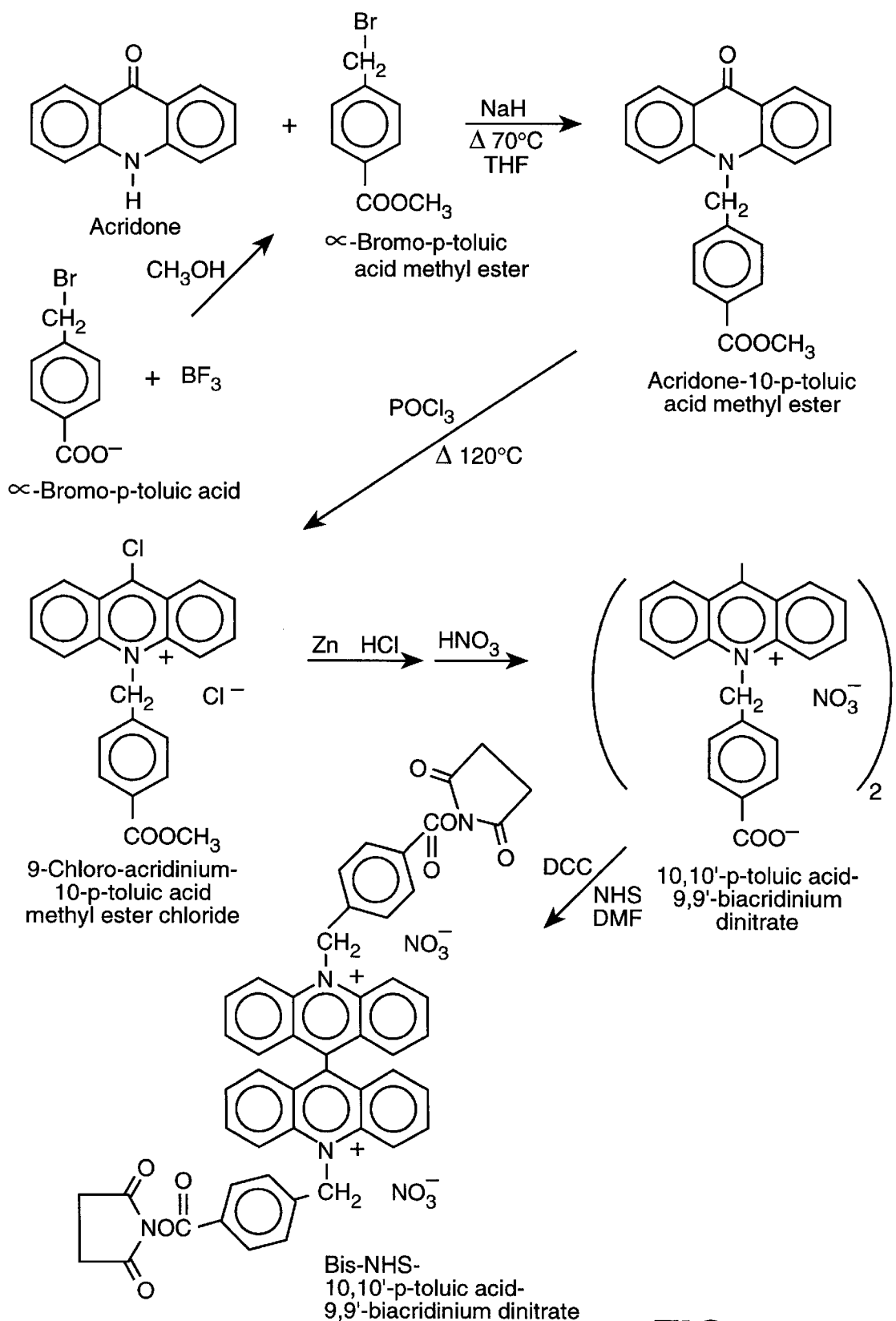
FIG._5

PREPARATION OF DERIVATIZED 10,10'-SUBSTITUTED-9,9'-BIACRIDINE LUMINESCENT MOLECULES AND SIGNAL SOLUTIONS

This is a continuation of application Ser. No. No. 08/265,481 filed Jun. 24, 1994 now abandoned.

TECHNICAL FIELD

The present invention relates to the synthesis of new 10,10'-substituted-9,9'-biacridinium derivatives, the preparation of novel chemical solutions for the production of light from these new molecules, and the use of these new molecules in luminescent reactions and assays. More particularly, the invention describes the synthesis of the N-Hydroxysuccinimide derivative of 10,10'-para-toluic acid-9,9'-biacridine and the demonstration of the ability to covalently bind (conjugate) this new molecule to another molecule such as an antibody and to produce measurable light from this bound chemiluminescent label molecule. The invention further involves a luminescent signal solution comprising at least one oxidant, a sulfoxide, a chelating agent, a reducing sugar, and an alcohol in aqueous sodium tetraborate to produce high yield photon emissions useful in chemical assays, nucleic acid assays and immunoassays.

BACKGROUND OF THE INVENTION

Measurement of light energy is becoming a very attractive method for monitoring the presence or concentration of substances in various media. Numerous bioluminescent and chemiluminescent reaction systems have been devised (Schroeder, et al., *Methods in Enzymology* 17:24–462 (1978); Zeigler, M. M., and T. O. Baldwin, *Current Topics In Bioenergetics,* D. Rao Sanadi ed., (Academic Press) pp. 65–113 (1981); DeLuca, M., *Non-Radiometric Assays: Technology and Application in Polypeptide and Steroid Hormone Detection,* (Alan R. Liss, Inc.) pp. 47–60 and 61–77 (1988); DeJong, G. J., and P. J. M. Kwakman, *J. of Chromatography* 492:319–343 (1989); McCapra, F. et al.,*J. Biolumin. Chemilumin.* 4:51–58 (1989); Diamandis, E. P., *Clin. Biochem.* 23:437–443 (1990); Gillevet, P. M., *Nature* 348:657–658 (1990); Kricka, L. J., *Amer. Clin Lab.,* November/December:30–32 (1990)).

Luminescence is the production of light by any means, including photoexcitation or a chemical reaction. Chemiluminescence is the emission of light only by means of a chemical reaction. It can be further defined as the emission of light during the reversion to the ground state of electronically excited products of chemical reactions (Woodhead, J. S. et al., *Complementary Immunoassays,* W. P. Collins ed., (John Wiley & Sons Ltd.), pp. 181–191 (1988)). Chemiluminescent reactions can be divided into enzyme-mediated and nonenzymatic reactions. It has been known for some time that the luminescent reactant luminol can be oxidized in neutral to alkaline conditions (pH 7.0–10.2) in the presence of oxidoreductase enzymes (horseradish peroxidase, xanthine oxidase, glucose oxidase), $H_2O_2$, certain inorganic metal ion catalysts or molecules (iron, manganese, copper, zinc), and chelating agents, and that this oxidation leads to the production of an excited intermediate (3-aminophthalic acid) which emits light on decay to its ground state, (Schroeder, H. R. et al.,*Anal. Chem.* 48:1933–1937 (1976); Simpson, J. S. A. et al., *Nature* 279:646–647 (1979); Baret, A., U.S. Pat. No. 4,933,276)). Other specific molecules and derivatives used to produce luminescence include cyclic diacyl hydrazides other than luminol (e.g., isoluminols), dioxetane derivatives, acridinium derivatives and peroxyoxylates (Messeri, G. et al., *J. Biolum. Chemilum.* 4:154–158 (1989); Schaap, A. P. et al., *Tetrahedron Lett.* 28:935–938 (1987); Givens, R. S. et al. *ACS Symposium Series* 383; Luminescence Applications, M. C. Goldberg ed., (Amer. Chem. Soc., Wash. D.C., pp. 127–154 (1989)). Additional molecules which produce light and have been utilized in the ultrasensitive measurement of molecules are polycyclic and reduced nitropolycyclic aromatic hydrocarbons, polycyclic aromatic amines, fluorescamine-labeled catecholamines, and other fluorescent derivatizing agents such as the coumarins, ninhydrins, o-phthalaldehydes, 7-fluoro-4-nitrobenz-2,1,3-oxadiazoles, naphthalene-2,3-dicarboxaldehydes, cyanobenz[f]isoindoles and dansyl chlorides (Simons, S. S., Jr. and D. F. Johnson,*J. Am. Chem. Soc.* 98:7098–7099 (1976); Roth, M., *Anal. Chem.* 43:880–882 (1971); Dunges, W., ibid, 49:442–445 (1977); Hill, D. W. et al., ibid, 51:1338–1341 (1979); Lindroth, P. and K. Mopper, ibid, 51:1667–1674 (1979); Sigvardson, K. W. and J. W. Birks, ibid, 55:432–435 (1983); Sigvardson, K. W. et al., ibid, 56:1096–1102 (1984); de Montigny, P. et al., ibid, 59:1096–1101 (1987); Grayeski, M. L. and J. K. DeVasto, ibid, 59:1203–1206 (1987); Rubinstein, M. et al., *Anal. Biochem.* 95:117–121 (1979); Kobayashi, S.-I., et al., ibid, 112:99–104 (1981); Watanabe, Y. and K. Imai, ibid, 116:471–472 (1981); Tsuchiya, H., *J. Chromatog.* 231:247–254 (1982); DeJong, C. et al., ibid, 241:345–359 (1982); Miyaguchi, K. et al., ibid, 303:173–176 (1984); Sigvardson, K. W. and J. W. Birks, ibid, 316:507–518 (1984); Benson, J. R. and P. E. Hare, *Proc. Nat. Acad. Sci.* 72:619–622 (1975); Kawasaki, T. et al., *Biomed. Chromatog.* 4:113–118 (1990)).

There are currently four known nonenzymatic systems: the acridinium derivatives (McCapra et al., British Patent No. 1,461,877; Wolf-Rogers J. et al., *J. Immunol. Methods* 133:191–198 (1990)); isoluminols, metalloporphyrins (Forgione et al., U.S. Pat. No. 4,375,972) and nonmetallic tetrapyrroles (Katsilometes, PCT International Publication No. WO 93/23756). These systems have certain advantages over the enzyme-mediated systems in that they have faster kinetics resulting in peak light output within seconds. The metalloporphyrins are small hapten molecules which decrease stearic hinderance problems in antigen binding. In addition, the metalloporphyrin molecules known to be luminescent are those containing a paramagnetic metal ion with emission yields above $10^{-4}$ (Gouterman, M., *The Porphyrins,* Vol. III, Dolphin, D., ed., (Academic Press): 48–50, 78–87, 115–117, 154–155 (1978); Canters, G. W and J. H. Van Der Waals, ibid, 577–578). It has also been known that metalloporphyrins, hyposporphyrins, pseudonormal metalloporphyrins and metalloporphyrin-like molecules such as metallic chlorins, hemes, cytochromes, chlorophylls, lanthanides and actinides undergo oxidation/reduction reactions which are either primary or secondary to structural perturbations occurring in the metallic center of these molecules and that their reactive ability to catalyze the production of chemiluminescence has been ascribed to the metallo center of these molecules (Eastwood, D. and M. Gouterman, *J. Mol. Spectros.* 35:359–375 (1970); Fleischer, E. B. and M. Krishnamurthy, *Annals N.Y. Academy of Sci.* 206:32–47 (1973); Dolphin, D. et al., ibid, 206:177–201; Tsutsui, M. and T. S. Srivastava, ibid, 206:404–408; Kadish, K. M. and D. G. Davis, ibid, 206:495–504; Felton, R. H. et al., ibid, 206:504–516; Whitten, D. G. et al., ibid, 206:516–533; Wasser, P. K. W. and J.-H. Fuhrhop, ibid, 206:533–549; Forgione et al., U.S. Pat. No. 4,375,972; Reszka, K. and R. C. Sealy, *Photochemistry and Photobiology* 39:293–299

(1984); Gonsalves, A. M. d'A. R. et al., *Tetrahedron Lett.* 32:1355–1358 (1991)). These reactions are altered by iron and other metal ions which may be present in the reactants and these metal ions can interfere with and greatly confound the assay of metalloporphyrin conjugate concentrations (Ewetz, L. and A. Thore, *Anal. Biochem.* 71:564–570 (1976)). Different metals will strongly influence the lifetimes and luminescent properties of the metalloporphyrins.

The nonmetallic porphyrin deuteroporphyrin-IX HCl has been shown to mediate the production of light from luminol in solution (Katsilometes, G. W., supra).

Use of the luminescent acridinium ester and amide derivatives in chemiluminescent reactions and in the development of nonisotopic ligand binding assays has been reported and reviewed (Weeks, I. et al., *Clin. Chem.* 29/8:1474–1479 (1983); Weeks, I. and J. S. Woodhead, *Trends in Anal. Chem.* 7/2:55–58 (1988)). The very short lived emission of photons (<5 sec) to produce the flash-type kinetics in the presence of $H_2O_2$ and NaOH oxidation reagents (pH 13.0) is characteristic of the system.

Methods of preparation of acridones and variously substituted acridines and acridones have been summarized (*Acridines,* Acheson, R. M. and L. E. Orgel, (Interscience Publishers, N.Y.) pp. 8–33, 60–67, 76–95, 105–123, 148–173, 188–199, 224–233 (1956)). Formation of biacridines by the combining of two acridine residues at the carbon-9 atom has been described and reviewed previously (Gleu, K. and R. Schaarschmidt, *Berichte* 8:909–915 (1940)). These efforts led to the synthesis of 10,10'-dimethyl, 10,10'-diphenyl and 10,10'-diethyl-9,9'-biacridinium nitrate molecules. It was also reported that these molecules will produce light when exposed to hydrogen peroxide in basic solution (Gleu, K. and W. Petsch, *Angew. Chem.* 48:57–59 (1935); Gleu, K. and R. Schaarschmidt, *Berichte* 8:909–915 (1940)).

The mechanism of light production by lucigenin (10,10'-dimethyl-9,9'-biacridinium nitrate) has been extensively studied and has been ascribed to a series of hydroxide ion nucleophilic additions to acridinium salts and their reduction products (pinacols), culminated by the oxidation of the main end product N-methylacridone (Janzen, E. G. et al., *J. Organic Chem.* 35:88–95 (1970); Maeda, K. et al., *Bul. Chem. Soc. Japan* 50:473–481 (1977); Maskiewicz, R. et al., *J. Am. Chem. Soc.,* 101/18:5347–5354 (1979); Maskiewicz, R. et al. ibid, 101/18:5355–5364 (1979)).

Modifications and derivatizations of 10-methyl acridine at the carbon-9 atom have led to the production of several useful chemiluminescent molecules having varying degrees of stability (Law, S.-J., et al., *J. Biolum. Chemilum.* 4:88–98 (1989)). These molecules produce a flash of light lasting less than five seconds when exposed to 0.5% w/v hydrogen peroxide in 0.1 mol/L nitric acid followed by a separate solution containing 0.25 mol/L sodium hydroxide.

A luminescent derivative, a luminescent derivatized molecule or a derivatized luminescent molecule as defined herein is a molecule which results from the covalent binding of a functional group or a group which changes the chemical reactivity and properties of a precursor molecule leading to the formation of a luminescent molecule suitable for conjugation to an analyte or a particular binding partner one wishes to use in assay development. A N-hydroxy succinimide derivatization of biacridines at one or both of the two 10,10' positions are the preferred luminescent derivatives of the invention. A compound or a molecule is a "derivative" of a first compound or first molecule if the derivative compound or molecule is formed (or can be formed) by reaction of the first compound or first molecule to form a new compound or new molecule either smaller or larger than the first compound or first molecule while retaining at least part of the structure of the first compound or first molecule. As used herein the term "derivative" can also include a "luminescent derivative".

Prior to this invention, synthesis of derivatized luminescent 10,10'-substituted-9,9'-biacridines has not been achieved. The previously known luminescent biacridines (e.g., lucigenin) contain no reactive group(s) which will permit the conjugation of the molecule to another. Until now, the biacridines have been of academic interest only and have been used to study the mechanism of light production and the interactions of reactive ionic species.

The use of luminescent reactions at the surface of light conductive materials (e.g., fiber-optic bundle) is the basis of the development of luminescent sensors or probes (Blum, L. J. et al., *Anal. Lett.* 21:717–726 (1988)). This luminescence may be modulated by specific protein binding (antibody) and can be produced in a microenvironment at the surface of the probe. The light output is then measured by photon measuring devices in the formulation of homogeneous (separation free) assays (Messeri, G. et al., *Clin. Chem.* 30:653–657 (1984); Sutherland, R. M. et al., *Complementary Immunoassays,* Collins, W. P., ed., (John Wiley & Sons, Ltd.) pp. 241–261 (1988)).

It has been demonstrated that charged synthetic polymers (poly-N-ethyl-4-vinylpyridinium bromide, PEVP) can completely inhibit the production of light by charged conjugate molecules through electrostatic interactions. This has particularly been studied in the enhanced luminol chemiluminescent reaction catalyzed by the negatively charged peroxidase enzyme. Addition of low-molecular-weight electrolytes will eliminate this inhibition thereby supporting an electrostatic nature of the observed effect (Valsenko, S. B. et al., *J. Biolum. Chemilum.* 4:164–176 (1989)).

Luminescent capillary electrophoresis gels, gel transfers or blots (Southern, Western, Northern and Dot) are examples of techniques which provide quantitative measurement of proteins and nucleic acid genetic material. These techniques can be used in conjunction with methods which amplify analyte expression, e.g., probes, PCR (polymerase chain reaction) bands, RFLP (restriction fragment length polymorphisms) methods and other methods which amplify gene expression and other analytes (Stevenson, R., *Biotech. Lab.* 8:4–6 (1990)).

It would be beneficial in improving assay sensitivity to increase the output of light obtained from chemiluminescent reactions by synthesizing biacridine molecules capable of producing superior quantities of photo emissions and by improving existing signal solutions and to have novel signal solutions which provide a greater intensity of light during chemiluminescent reactions. The ability to modulate the kinetics of light output through manipulation of the signal solution formula is particularly beneficial in tailoring assays for a variety of uses (genetic probe, sensor, hormones, etc.).

SUMMARY OF THE INVENTION

One aspect of the invention is the method for detecting the presence of a biacridine luminescent derivative in a sample. The method comprises contacting the sample with a signal solution to produce, by means of chemiluminescence, measurable emitted light and measuring the emitted light with a photometric instrument or device.

Another aspect of this invention is methods for the synthesis of luminescent derivatized 10,10'-substituted-9,9'- biacridine molecules which can be bound to an analyte or to a binding partner of an analyte or to a ligand of a binding partner to an analyte. These molecules may have additional substitutions at other sites on the molecule such as carbon atoms one through eight.

Still another aspect of the invention is directed to a chemiluminescent system for emitting measurable light useful in a chemical assay, a ligand binding assay, an immunoassay or a nucleotide assay. The system comprises, at a pH ranging from about 10.0 to about 14.0, a 10,10'-substituted-9,9'-biacridine with a specific energy of activation and oxidation potential, bound to an analyte, or to a binding partner of an analyte or to a ligand of a binding partner to an analyte and an oxidant or a combination of oxidants capable of overcoming the inherent oxidation potential of the biacridine. In this system the biacridine acts as a luminescent label (trigger or tag) for the production of chemiluminescence in chemical assays, homogeneous, heterogeneous competitive and sandwich immunoassays, ligand binding assays and nucleotide assays. The light is produced upon exposure of the biacridine label to a signal solution having the nucleophilic reactants and oxidant or oxidants.

The 10,10'-substituted-9,9'-biacridines are especially beneficial as the label is more sensitive (i.e., detects smaller quantities of analyte) than known chemiluminescent labels and are able to undergo modification of the kinetics of light production through manipulation of the signal solution formula resulting in stable light producing kinetics for at least 0.1 second and also for as long as 6 seconds.

A further aspect of the invention is a method for the synthesis of novel 10-substituted biacridines which have powerful luminescent properties. This method involves the esterification of the substituent, the alkylation of the starting material (acridone), dimerization of this molecule and derivatization (if necessary) with N-Hydroxysuccinimide.

Another aspect of the invention is a chemiluminescent signal solution which when reacted with a chemiluminescent label that is a luminescent molecule produces chemiluminescence. The signal solution comprises at a pH from about 10.0 to about 14.0, 0.02M sodium tetraborate (borax), ethylenediaminetetra-acetic acid (EDTA), dimethyl sulfoxide (DMSO), D(−) fructose, potassium superoxide ($KO_2$) and 2-Methyl-2propanol. Where the chemiluminescent label is an acridinium derivative, lucigenin, a lucigenin luminescent derivative, a biacridine, a biacridinium luminescent derivative, a cyclic diacyl hydrazide or a pteridine the reaction will produce a signal to noise photon emission ratio of at least 20:1 at 1 ng/ml of label concentration for at least 0.1 seconds duration. Depending upon the label and the variation of the concentration of the signal solution components, the signal ratio can be 50:1, 100:1, 200:1, 500:1, and even 700:1 and greater at 1 ng/ml of label concentration. The emission can also be manipulated to last up to 6 seconds or longer.

It has also been demonstrated that this signal solution can trigger acridinium derivative, lucigenin and 10,10'-substituted-9,9'-biacridine chemiluminescence producing a significant increase in light output and a change in light output kinetics from the output obtained with previously known signal solutions.

BRIEF DESCRIPTION OF THE DRAWINGS

FIG. 1 is a histogram that represents the results of an experiment which compares the relative chemiluminescence of the signal reagent (zero), lucigenin and 10,10'-para-toluic acid-9,9'-biacridine when flashed with the signal solution of the invention.

FIG. 2 is a chart representing the results from a scanning spectrophotometric measurement of the label of the invention when conjugated to antibody.

FIG. 3 is a curve representating the linearity of signal obtained when flashing a 10,10'-substituted-9,9'-biacridine labeled antibody with the signal solution of the invention.

FIGS. 4A and 4B show the variability in light output kinetics obtained with varying formulations of the signal reagent of the invention.

FIG. 5 is a schematic flow diagram of a preferred method for synthesizing the N-Hydroxysuccinimide derivative of 10,10'-para-toluic acid-9,9'-biacridine dinitrate.

DETAILED DESCRIPTION OF THE INVENTION

Although the words and terms in this application have their normal definitions, the following definitions apply to preferred embodiments of the invention.

As defined herein, a signal solution comprises a reagent or group of reagents which, when combined with a specific luminescent molecule or a specific luminescence mediating molecule, will cause the production of light. A luminescent label or tag as described herein is a substance bound to an analyte, a binding partner of an analyte, or to a ligand of a binding partner of an analyte either directly (e.g., covalently) or indirectly (e.g., by means of a specific binding substance (protein), a biotin-avidin or biotin-streptavidin bridge) which when combined with a signal solution either produces light or causes light to be produced. A luminescent label is a luminescent molecule (i.e., the substance which emits light).

As defined herein, a luminescent molecule is a substance, which following electronic excitation by constituents of a chemical solution, will emit a photon(s) upon decay of orbital electrons to ground state.

As used herein, a luminescent reactant is a free luminescent molecule (i.e., a luminescent molecule that is not bound to an analyte, a binding partner of an analyte or to a ligand of a binding partner of the analyte). Also as used herein the singular term "luminescent molecule" can also include the plural "luminescent molecules". Also, as used herein, the singular term "luminescence mediating molecule" can also include the plural.

As used herein, the signal solution is comprised of free molecules (i.e., not bound to an analyte, a binding partner of an analyte or to a ligand of a binding partner of the analyte). Also as used herein the singular term "luminescent molecule" can also include the plural "luminescent molecules". Also, as used herein, the singular term "luminescence mediating molecule" can also include the plural.

The invention is directed to methods for synthesizing luminescent 10,10'-substituted-9,9'-biacridine derivative molecules which can be bound to an analyte, a binding partner of an analyte, or to a ligand of a binding partner of an analyte either directly or indirectly.

The invention is also directed to a method for detecting in a sample the presence of a 10,10'-substituted-9,9'-biacridine luminescent derivative having a specific energy of activation and oxidation potential. The method comprises contacting the sample with a signal solution which comprises at least one oxidant capable of lowering the specific energy of activation or oxidation potential of the 10,10'-substituted-9, 9'-biacridine. The 10,10'-substituted-9,9'-biacridine and the oxidant react to produce emitted light by means of chemiluminescence. Postulated mechanisms for the chemiluminescent production of light by 10,10'-substituted-9,9'-biacridines would begin with the addition of nucleophiles such as hydroxide ions to the biacridine leading to schism of the dimer between the 9,9'-carbon atoms. This schism produces two N-Methylacridone molecules which can be oxidized to produce light as discussed by Janzen, et al., Maeda, et al., and Maskiewicz, et al., supra. Abstraction of an electron from an appropriate luminescent molecule leads to the formation of the excited intermediate which emits a photon upon decay of the luminescent molecule to the ground energy state. The light is then measured preferably with a photometric instrument or device such as the Berthold Lumat LB 950 luminometer. This method is more sensitive and more accurate due to lack of interference and self absorption problems encountered with the usual fluorometric methods used to detect fluorophores in solution.

Potassium superoxide is preferred for overcoming the oxidation potential of the 10,10'-substituted-9,9'-biacridine. However, potassium superoxide in conjunction with other oxidants such as osmium tetroxide or hydrogen peroxide, is also another oxidant mixture capable of overcoming the inherent oxidation potential of the 10,10'-substituted-9,9'-biacridine.

The invention is also directed to a chemiluminescent system for emitting measurable light useful in a chemical assay, in a ligand binding assay such as an immunoassay or in a nucleotide assay. This system comprises at a pH ranging from about 10.0 to about 14.0, a 10,10'-substituted-9,9'-biacridine luminescent derivative having an oxidation potential bound to an analyte or to a binding partner of an analyte or to a ligand of a binding partner to an analyte, and at least one oxidant which is/are capable of lowering the oxidation potential of the 10,10'-substituted-9,9'-biacridine. Essentially the 10,10'-substituted-9,9'-biacridine acts as a label (i.e., a tag or tracer) and produces light in the chemiluminescent reaction. The immunoassay may be homogeneous or heterogeneous and a competitive or sandwich assay. The light is produced by the 10,10'-substituted-9,9'-biacridine by means of chemiluminescence upon exposure of the 10,10'-substituted-9,9'-biacridine to an oxidant or oxidants.

This system is particularly useful for detecting an analyte such as a nucleic acid, an antibody, an antigen, a hapten or hapten conjugate, a macromolecule, a protein or a polymer. A binding partner to an analyte in this system may be a nucleotide probe, an antibody, an antigen, a hapten, a hapten conjugate, a macromolecule, a protein or a polymer.

A ligand used herein means a linking or binding molecule and may include an antigen, an antibody, a hapten, a hapten conjugate, a macromolecule, a protein or a polymer other than a protein such as a polyhydrocarbon, a polyglyceride or a polysaccharide.

A hapten conjugate as used herein is a small molecule (i.e., a molecule having a molecular weight of less than 6,000 Daltons) that is attached to another molecule. A particularly suitable hapten conjugate is a steroid molecule-10,10'-substituted-9,9'-biacridine conjugate. The analyte may be bound to the binding partner or the binding partner may be bound to the ligand by means of a biotin-avidin or a biotin-streptavidin bridge. The ligand may also be biotin, avidin or streptavidin and the analyte may also be bound to the 10,10'-substituted-9,9'-biacridine by means of the biotin-avidin, biotin-streptavidin system. The system provides great sensitivity (up to $10^{-16}$ to $10^{-20}$ molar detection of antibody or antigen) when the system comprises 10,10'-substituted-9,9'-biacridine luminescent label and potassium superoxide as the oxidant. An even greater sensitivity (up to $10^{-22}$ molar detection of antibody or antigen) is obtained when the system comprises a chelating agent, DMSO, D(−) fructose, 2Methyl-2-propanol, aqueous sodium tetraborate and a combination of oxidants capable of overcoming the oxidation potential.

While the chemiluminescent system will be effective at a pH ranging from about 10 to about 14, the preferred pH is from a pH of about 12.5 to 13.5.

The chemiluminescent properties of the 10,10'-substituted-9,9'-biacridine tag together with the other reagents in the system make the system particularly suitable for the development of ultrasensitive assays for many hapten and macromolecular analytes to which the 10,10'-substituted-9,9'-biacridine can be directly or indirectly conjugated such as hormones, vitamins, toxins, proteins, infectious and contagious agents, chemicals, drugs, tumor markers, receptors, biotin, avidin, streptavidin and genetic material. The 10,10'-substituted-9,9'-biacridine can also be directly or indirectly conjugated to a specific binding protein such as an antibody for use in chemiluminometric assay development.

The invention is further directed to a chemiluminescent system for emitting measurable light useful in a chemical assay, an immunoassay, a ligand binding assay or a nucleic acid assay which comprises a 10,10'-substituted-9,9'-biacridine having a specific oxidation potential, bound to an analyte, or to a binding partner of an analyte or to a ligand to a binding partner to an analyte and a signal solution which comprises, at a pH ranging from about 10.0 to about 14.0, the oxidant, potassium superoxide, or a combination of oxidants comprising osmium tetroxide and potassium superoxide.

Examples of luminescent molecules for use with the signal solution in this invention are the acridinium derivatives, pteridines, pteridine derivatives, lucigenin, lucigenin derivatives, luciferin, luciferin derivatives, cyclic diacyl hydrazides (luminol or isoluminol), an acridinium derivative such as dimethyl acridinium ester or luciferin and lucigenin derivatives such as those resulting from N-hydroxy succinimide derivatizations are preferred.

Again, this chemiluminescent system lends itself to heterogeneous and homogeneous assays including competitive and sandwich immunoassays. The sensitivity of the system is extremely high when the signal solution comprises the EDTA, DMSO, D(−) fructose, at least one oxidant, 2-Methyl-2-propanol and aqueous sodium tetraborate as described above. Again, the analyte may be a nucleic acid, an antigen, an antibody, a hapten, a hapten conjugate, a macromolecule, a protein or a polymer. The homogeneous assay would involve the use of inhibitors of label luminescence such as polyions. A polycation such as poly(4-vinylpyridinium dichromate) would inhibit, for example, an unbound deuteroporphyrin IX dihydrochloride (DPIX) labeled compound while a polyanion such as poly (vinylalkyl) would inhibit an unbound positively charged 10,10'-substituted-9,9'-biacridinium labeled compound. Unbound in this instance of an assay means that if, for example, the compound is an antigen-label conjugate, it is not bound to, for example, an antibody or if the compound is an antibody-label conjugate it is not bound to an antigen, etc.

The invention is also directed to a method for using a 10,10'-substituted-9,9'-biacridine in a chemiluminescent heterogeneous assay for detecting the presence of dual analytes in a sample. Suitable analytes for detection are nucleic acids, antibodies, antigens, haptens, hapten conjugates, macromolecules, polymers or proteins. Again, the method can be a chemical assay, a nucleotide assay or a ligand binding assay such as an immunoassay. The method may also be a combination of any of these assays. The invention involves the conjugation of 10,10'-substituted-9,9'-biacridine tag to a first analyte or to a binding partner of that analyte or to a ligand of a binding partner of that analyte and the binding of a different tag or label such as a nonmetallic tetrapyrrole luminescent molecule or a molecule that mediates chemiluminescence such as an enzyme to a second analyte or to a binding partner of the second analyte or to a ligand of the binding partner of the second analyte. The analytes may be a polynucleotide strand, a chemically active compound such as chlorin $e_6$ or an immunologically active compound such as an antibody, an antigen, a hapten, a hapten conjugate, a macromolecule, a protein or a polymer.

Generally, in the dual sandwich-type immunoassay, a binding partner to one site on the first analyte is attached to a solid phase such as glass, polypropylene, polycarbonate or polystyrene and the, thus, coated solid phase is contacted with the sample and second binding partner for a second site on the analyte. The second binding partner is conjugated to the label (e.g., the 10,10'-substituted-9,9'-biacridine derivative). The same situation exists for the second analyte only the label and the binding partners are naturally different. The solid phase is washed and the bound conjugates are exposed to the appropriate signal solution or signal solutions. Generally, in a competitive assay, the solid phase is coated with limited concentrations of binding partners specific for each analyte of interest. The solid phase is then contacted with the sample and with a measured amount of first analyte conjugated to the 10,10'-substituted-9,9'-biacridine and with a measured amount of second analyte conjugated to the other luminescent label. Following contact, the solid phase is washed to remove any unbound conjugate. With both the sandwich-type or competitive-type assay, the washed solid phase may be separately treated first with a signal solution specific for only one of the two labels wherein the label and the solution react to produce emitted light and the amount of analyte related to that specific label may be determined by measuring the amount of light emitted, the solid phase can then be separately contacted with another chemiluminescent signal solution specific for the second label or tag relating to the other analyte whereby that label and signal solution react to produce emitted light. Again, the measurement of the light from the second reaction will determine the amount of second analyte present in the sample.

Since the light produced as a result of the two different labels has different properties (i.e., the wavelength of light given off by means of each label may differ or the actual amount of light produced per second of reaction may differ between the two labels), it is possible to treat the washed phase with a signal solution which will produce light by both conjugates simultaneously, differentiate that light and measure the light to determine the amount of each analyte in the sample. One can differentiate the light given off as a result of the two different labels by utilizing time resolved luminescent analysis such as that used in fluorometry (Lovgren, T. and K. Pettersson, *Luminescence Immunoassay and Molecular Applications,* Van Dyke, K. and R. Van Dyke eds., CRC Ress, Boca Raton, Ann Arbor, Boston, Mass., pp. 233–254 (1990)).

The differences in emission properties such as wavelengths can also be utilized (Kleinerman, M. et al., *Luminescence of Organic and Inorganic Materials,* Kallmann, H. P. and G. M. Spruch eds., International Conference, New York University Washington Square, sponsored by Air Force Aeronautical Research Laboratory, Army Research Office, Curham Office of Naval Research, N.Y.U., pp. 197–225 (1961)).

A preferred luminescent label for the dual analyte assay with a biacridinium derivative is an acridinium derivative such as dimethyl acridinium ester or a nonmetallic tetrapyrrole but several other luminescent labels previously discussed are also suitable. A preferred nonmetallic tetrapyrrole is DPIX. The preferred signal solution for producing emitted light by means of the DPIX label comprises at a pH from about 10.0 to about 14.0, trans,trans-5-(4-Nitrophenyl)-2,4-pentadienal, sodium di-2-ethylhexyl sulfosuccinate, the luminescent reactant luminol, glucose, benzyltrimethylammonium hydroxide, cumene hydroperoxide, trisodium para periodate, potassium superoxide and EDTA. The signal solution best suited for flashing the bound 10,10'-substituted-9,9'-biacridine comprises at a pH from about 10.0 to about 14.0 in 0.02 borax, EDTA, DMSO, D(−) fructose, potassium superoxide, 2-Methyl-2-propanol and aqueous sodium tetraborate. If one of the analyte conjugates is an enzyme labeled analyte conjugate the substrate for that enzyme can be included in the signal solution.

In addition, the invention is directed to a chemiluminescent homogeneous assay for detecting dual analytes in a sample. In a competitive-type assay, the solid phase is coated with a binding partner specific for each different analyte. The solid phase may additionally be coated with a luminescent reactant in cases where a tetrapyrrole is used as one of the labels. The thus coated solid phase is then contacted with the sample, with a known amount of one of the analytes conjugated to a 10,10'-substituted-9,9'-biacridine label, with a known amount of the other analyte conjugated to a luminescent label other than the biacridine and with a polyion (such as poly-N-ethyl-4-vinylpyridinium bromide, poly-4-vinylpyrimidinium dichromate, polyvinylchloride, poly(vinylalcohol), or poly(vinylbenzyl chloride) capable of inhibiting unbound biacridine luminescent label conjugate such as anti-TSH-10,10'-substituted-9,9'-biacridine by preventing the overcoming of the oxidation potential of the luminescent label of the unbound conjugate (Vlasenko, S. B. et al, *J. Biolum. Chemilum.* 4:164–176 (1989)). In an assay where it is necessary to inhibit unbound luminescent label antibody conjugate such as DPIX antibody conjugate a polycation can be used. Following contact, the solid phase is then treated with a signal solution capable of either producing emitted light by means of both conjugates simultaneously or separately contacting the solid phase with a signal solution specific for one label and measuring the emitted light and then separately contacting the solid phase with a signal solution specific for emitting light by means of the label of the other conjugate.

The invention is additionally directed to a chemiluminescent signal solution which comprises at a pH ranging from about 10.0 to about 14.0 an aqueous solution of about 150 mM to about 450 mM potassium superoxide, preferrably 300 mM in a buffered solution. The preferred buffer is sodium tetraborate but other solutions such as trizma base and boric acid also work well. The preferred luminescent molecules for use as labels in conjunction with this signal solution are the acridinium and 10,10'-substituted-9,9'-biacridine derivatives. However, isoluminol alone and deuteroporphyrin IX●2HCl in conjunction with the luminescent reactant luminol when used with the $KO_2$ signal solution are also suitable labels. When the $KO_2$ in a buffered signal solution is reacted with a luminescent molecule such as 10,10'-substituted-9,9'-biacridine or a derivative thereof or a luminescent label conjugate such as estradiol 17β-10,10'-substituted-9,9'-biacridine or anti-TSH-10,10'-substituted-9,9'-biacridine, a signal to noise photon emission ratio of at least 20:1 at 1 ng/ml of label concentration is produced for at least 0.1 seconds. Depending upon the label the signal ratio can be 50:1, 100:1 or 200:1 and greater at 1 ng/ml of label concentration using this signal solution and a variety of biacridine labeled conjugates. The emission can also be manipulated to last from up to 6 seconds or longer.

The invention is further directed to a chemiluminescent signal solution which comprises at a pH from about 10.0 to about 14.0, 0.02M aqueous borax, EDTA, DMSO, D(−) fructose, potassium superoxide, and 2-Methyl-2-propanol. This signal solution can trigger 10,10'-substituted-9,9'-biacridine derivative conjugate chemiluminescence producing a significant increase in light output and a change in light output kinetics from the output obtained with previously known signal solutions. When this solution is reacted with a luminescent label or a luminescent label conjugate such as 10,10'-substituted-9,9'-biacridine-antibody or anti-TSH-10,10'-substituted-9,9'-biacridine, a signal to noise photon emission ratio of 500:1 at 1 ng/ml of label concentration is produced for at least 0.1 seconds (see FIG. 3). Again, the signal ratio can be 50:1, 100:1 and even 700:1 and greater at 1 ng/ml of label concentration depending upon variations in the solution and the particular labeled conjugate. The emission can also be manipulated to last from up to 6 seconds or longer.

In addition, the invention is directed to a signal solution which comprises, at a pH ranging from about 10.0 to about 14.0, in an aqueous borax solution, EDTA, DMSO, D(−) fructose, potassium superoxide and 2-Methyl-2-propanol. It is preferred in all aspects of the invention where this signal solution is used that it be prepared according to the procedure described in Example 2 with respect to components, sequence of component addition and component concentration. However, the components may be added in an altered sequence and other component concentrations which are also suitable are:

Borax: 0.005–0.05M of aqueous buffer solution
EDTA: 0.002–0.2 mM
DMSO: 0–8 μl/ml of the above borax buffer solution
D(−) fructose: 2–10 mg/ml of buffer solution
Potassium Superoxide: 210–365 mM
2-Methyl-2-propanol: 0.05–0.25 ml/ml of buffer solution When this solution is reacted with a luminescent label such as a 10,10'-substituted-9,9'-biacridine, the luminescent reactant produces a signal to noise photon emission ratio of at least 300:1 at 1 ng/ml of luminescent label. Again, depending upon the label the signal ratio can be 50:1, 100:1, 200:1, etc. at 1 ng/ml of label concentration. The emission can also be manipulated to last from up to 6 seconds or longer.

EXAMPLE 1

Synthesis of 10,10'-Substituted-9,9'-Biacridine Derivatives

This approach to the synthesis of derivatized luminescent biacridine molecules included the synthesis of acridone by the cyclisation of diphenylamine-2-carboxylic acids and N-benzoyldiphenylamine- 2-carboxylic acids as described by Acheson and Orgel, supra. (All chemicals and solvents can be obtained from Sigma/Aldrich, St. Louis, U.S.A. and Pacific Pac Inc., Hollister, Calif.). Acridone can also be purchased from Sigma/Aldrich.

In addition to the preparation of acridone, a methyl ester of a substituent molecule was synthesized for covalent attachment at the 10-carbon atom of acridone. A substituent molecule for derivatizing biacridine molecule as used herein is a molecule having a functional group that provides for the further derivatization of the biacridine or for the attachment of the biacridine to other molecules such as antigens, antibodies, etc. Usually the substituent molecule used in the course of the invention has a molecular weight of about 10,000 or less. In this example, the methyl esterification of the substituent molecule alpha-bromo-para-toluic acid was carried out. Other molecules having good leaving group(s) (such as halogen atom(s)) at one end of the molecule and the presence of functional group(s) elsewhere on the molecule, can also serve as substituent molecules and be successfully esterified. A good example of another substituent molecule of this type is iodoacetic acid. Esterification was accomplished by reacting the substituent molecule in 10% boron trifluoride in methanol (25 ml of boron trifluoride-methanol per gram of substituent molecule was preferably added. This was allowed to react for at least 10 hours at room T° and the methyl ester was extracted with methylene chloride in a separation funnel. The extract was washed twice with $H_2O$, once with 0.1M sodium bicarbonate and twice again with $H_2O$. The volume was reduced to dryness at 60° C. on a rotavapor RE120 rotary evaporator. Alternate methods of methyl ester synthesis are the use of ether followed by the addition of diazomethane and the use of methanol containing 5% concentrated sulfuric acid.

The next step in the synthesis was the alkylation of acridone. To accomplish this, 5.4 mM of acridone and 6.5 mM of sodium hydride were added to 100 ml anhydrous tetrahydrofuran (THF). This mixture was then refluxed with stirring for 2 hours at 70° C. under argon gas. To this mixture was added 5.5 mM of the substituent methyl ester (e.g. alpha-bromo-paratoluic acid methyl ester) and the combination was refluxed with stirring at 70° C. for 10–13 hours. Silica gel thin layer chromatography (Baker Chemical Co., Phillipsburg, Pa.) at this time with 2% methanol in methylene chloride revealed a spot with $R_f=0.2$ for hydrolyzed acridone-10-substituent; a second spot at $R_f=0.4$ for unreacted acridone; a third spot (very small) at $R_f=0.5$ for unknown byproduct; a fourth spot at $R_f=0.6$ for the acridone-10-substituent methyl ester (acridone-10-para-toluic acid methyl ester); and a fifth spot at $R_f=0.9$ for unreacted substituent-methyl ester. The reaction mixture was a light lemon-brown color containing a precipitate (ppt.). The ppt. (containing mostly hydrolyzed acridone-10-substituent) was filtered off and discarded. The filtrate was extracted with ethyl acetate and water in a separation funnel to remove remaining salts and hydrolyzed material. The impurities remained in the aqueous phase. The volume of the organic phase (ethyl acetate phase) was reduced to dryness on a rotaevaporator at 60° C. Methylene chloride was then added and the unreacted (insoluble) acridone precipitate was filtered off. The methylene chloride extract was then eluted and purified on a silica-60 column with 3% ethyl acetate in methylene chloride. The acridone-10-para-toluic acid methyl ester was eluted and contained within the first yellow band.

This material was again concentrated on a rotaevaporator with replacement of the ethyl acetate-methylene chloride eluant by methanol (through a continuous feed tube on the rotaevaporator). The purified acridone-10-substituent methyl ester precipitated as a light yellow crystalline material. This precipitate was filtered and washed with methanol (yield approximately 50%). These molecules and their acid precursors were active fluorophores with (for examples) acridone-10-para-toluic acid and its NHS derivative exciting at 403 nm and emitting at 440 nm; and acridone-10-acetic acid and its NHS derivative exciting at 398 nm and emitting at 438 nm.

Acridone-10-substituted intermediates (e.g., acridone-10-acetic acid) were also directly synthesized by mixing well together 8.45 g of 2-chlorobenzoic acid, 7.80 g N-phenylglycine, 11.00 g anhydrous potassium carbonate and 0.30 g Cu++ powder in 6 ml $H_2O$. This mixture was then refluxed overnight over an oil bath at 160° C. Ethanol was added slowly and the product was dissolved in water, filtered and ppt. with HCl. The whole mixture was refiltered to remove unconsumed 2-chlorobenzoic acid and the remaining oil in that filtrate allowed to crystalize. The filtrate was dissolved in NaOH, filtered, acetic acid was added and the mixture was refiltered to remove further unreacted 2-chlorobenzoic acid. The product was precipitated by the addition of HCl (acid product) and dried. Then it was extracted with excess benzene and further purified by dissolving in sodium acetate solution, boiling with activated charcoal and reprecipitating with HCl. The pure product was again filtered and crystallized from dilute methanol to give a white ppt. (mp. 165°–167° C.).

Acridone-10-substituted molecules (e.g., acridone-10-acetic acid) were also synthesized, by refluxing a mixture of 500 mg (2.7 mM) acridone, 130 mg 80% NaH in mineral oil and 50 ml anhydrous THF under argon for 2–4 hours. Iodoacetic acid (540 mg, 2.7 mM) was then added and refluxing of the mixture was continued under argon for an additional 10 hours. The ppt. was filtered and the filtrate was purified on a reverse phase column under 20–30% ethanol elution. This purified material was then dried and taken up in THF and hydrolyzed with 4 N NaOH for 10 hours. Water was added and the mixture was filtered. The filter was washed with $H_2O$, and the mixture was brought to a pH of 8.0 with 1 N HCl. Final purification was performed on reverse phase silica gel column with 10 to 30% methanol in water. The volume was reduced on a rotaevaporator (e.g., RE120) and reprecipitation was carried out with 1 N HCl overnight at pH 2.5. The product was collected by centrifugation and washed with water once. It was dried on a lyophylizer (yield approximately 40%).

Conversion of the acridone-10-para-toluic acid methyl ester to the quaternized 9-chloro-acridinium-10-paratoluic acid methyl ester was accomplished by reacting the acridone-10-substituent methyl ester with phosphorous oxychloride ($POCl_3$). One milliliter of $POCl_3$ was added to each 50 mg of the purified methyl ester and this mixture was refluxed for 1 hour over an oil bath at 120° C.

Dimerization and de-esterification of the 9-chloro-acridinium 10-para-toluic acid methyl ester was accomplished by the addition of 1 g of cold zinc metal and 10 ml of freezing cold concentrated HCl/100 mg of 9-chloro-acridinium-10-para-toluic acid methyl ester which was allowed to react under freezing conditions for anywhere from 1 to 10 hours. This reaction is violent and must be carried out under freezing conditions for 1–10 hours. The ppt. was then filtered off and washed with water. Purification of the acid filtrate was accomplished on a silica gel C-18 reverse phase column. The column was pretreated with methanol followed by 0.1N nitric acid followed by 0.01M phosphate buffer. Elution of the filtrate was first accomplished with methanol in 0.01M phosphate buffer to remove the byproducts, unreacted materials and salts. The product, (10,10'para-toluic acid-9,9'-biacridine salt, a disubstituted biacridine) which sticks to the top of the column, was then eluted with 30 to 90% methanol in 0.1N nitric acid (the methanol strength should be increased from 30% to 90% to remove all product). Product eluted as a yellow band with approximately 50% methanol in 0.1N nitric acid. The protonated purified dimer-dinitrate salt (10,10'-para-toluic acid-9,9'-biacridinium dinitrate) was then concentrated on a rotaevaporator at 60° C. to a small volume (5 ml) and was lyophylized to dryness. Scanning spectrophotometry on a Perkin-Elmer 552 Spectrophotometer revealed a characteristic absorbance with a preliminary shoulder at 460 nm, a first peak at 435 nm, a second shoulder at 415 nm, a major peak at 370 nm and a trailing shoulder at 355 nm (see FIG. 2). NMR plot on a Bruker ARX 400 instrument (Rheinstetten-OF, Germany) gave a peak at 3.9 ppm indicating the presence of the methylene carbon attached to the 10 position nitrogen on the dimer and the presence of multiple aromatic carbon peaks in the 7 to 9 ppm range.

Further derivatization of the dimer with N-hydroxysuccinimide (NHS) was accomplished by adding (with stirring) 211 micromoles (uM) of dicyclohexylcarbodiimide to 141 uM of the dimer in dry dimethylformamide (DMF) (0.5 ml/mg of dimer). To this was added 211 uM of N-Hydroxysuccinimide which was allowed to react at room T° for 10 hours. Urea precipitates which formed during this reaction were filtered off. This NHS-ester of the label is very stable in an amber vial (at least one year). On reverse phase TLC the major peak did not move on elution with 90% methanol in 0.01M phosphate buffer (a yellow spot at the origin under long wavelength U.V. light), but does move with an $R_f$=0.2 in 0.1 nitric acid/70% methanol (v/v).

Conjugation of the 10,10'-para-toluo-NHS-9,9'-biacridinium dinitrate derivative to antibody began with the addition of 100 microliters of the DMF solution of the derivative to 1 mg of the antibody in PBS at pH 7.4. In this example polyclonal antibody to the beta-chain of thyroid stimulating hormone was conjugated, however, any antibody, analyte, polymer or binding protein can be utilized. This mixture was allowed to react at room T° for 10 hours and then 54 microliters of a 1 mg/ml solution of d-L-lysine was added to the antibody-derivative mix and was allowed to react for an additional 3 hours. This step is necessary for occupying unreacted NHS sites on the luminescent derivative-antibody conjugate.

This antibody-10,10'-substituted-9,9'-biacridine conjugate was purified on a 20 cm Biogel P-10 column (BioRad; Hercules, Calif.) by eluting with a buffer containing 10 mM dibasic potassium phosphate and 0.1M NaCl at a pH of 7.4. The antibody conjugate eluted in the first fraction off the column which can be monitored by TLC and spectrophotometry. The antibody conjugate had two spectrophotometric peaks at 365 nm (small peak for the label) and at 275 nm for the antibody and was successfully flashed with the signal solution of the invention described in Example 2 resulting in very rapid light emission kinetics (see FIG. 4).

A mildly acidic environment (0.01 N $HNO_3$) stabilizes the labels and also gives the strongest signal to noise ratio. A wash solution containing 0.2 microliters Tween-20/ml PSS brought to 0.01N with $HNO_3$ should work well in separation-required assays. Exposing the label to 5 microliters of the final wash solution just before flashing may also enhance the signal.

EXAMPLE 2

Preparation of Signal Solution

The signal solution for the production of light from the new chemiluminescent molecules was formulated as follows:

To each 100 ml of 0.02M sodium tetraborate was added the following with stirring:
 a) 0.744 mg (0.02 mM) ethylenediaminetetraacetic acid (EDTA)
 b) 100 ul of dimethylsulfoxide (DMSO)
 c) 400 mg (0.02M) D(-) fructose
 d) 1996 mg (280 mM) potassium superoxide ($KO_2$)
 e) 17 ml 2-Methyl-2-propanol

EXAMPLE 3

Assay Comparing 10,10'-para-toluic acid-9,9'-Biacridinium Dinitrate and bis-N-Methylacridinium Dinitrate (Lucigenin)

As shown in FIG. 1 this example compared the signal obtained with signal solution only (Bar 1), a 1.9 nanomolar concentration of lucigenin in distilled $H_2O$ (Bar 2), and a 1.3 nanomolar concentration of 10,10'-para-toluic acid-9,9'-biacridinium dinitrate in distilled $H_2O$ (Bar 3). The signal solution was prepared according to Example 2, infra. The conditions for this assay were the addition of 300 microliters of signal solution to 5 µl of water in triplicate to 12×75 mm polystyrene tubes (VWR Scientific Inc., Philadelphia, Pa.) to obtain the zero signal. The signal of each chemiluminescent molecule was obtained by flashing 5 µl of the diluted label with 300 µl of signal solution in triplicate in a Berthold Lumat.

EXAMPLE 4

Assay Demonstrating the Linearity of Signal With Increasing Dilutions of Anti-TSH-10,10'-para-toluo-9,9'-biacridine Conjugate As shown in FIG. 3 this example demonstrated the chemiluminescent functionality of the antibody conjugate and the linearity of signal with increasing dilutions. The anti-TSH-10,10'-para-toluo-9,9'-biacridine conjugate was diluted from $10^{-9}$ g/ml to $10^{-18}$ g/ml and 5 µl of each dilution was flashed with 200 µl of signal reagent in triplicate in a Berthold Lumat and the magnitude of the signal was recorded. The results were as follows: $10^{-9}$ g/ml-12,000,000 counts/sec; $10^{-12}$ g/ml-570,000 counts/sec; $10^{-13}$ g/ml-37,119 counts/sec; $10^{-14}$ g/ml-3,510 counts/sec; $10^{-15}$ g/ml-556 counts/sec; $10^{-16}$ g/ml-304 counts/sec; $10^{-17}$ g/ml-240 counts/sec; $10^{-18}$ g/ml-229 counts/sec; 0.0 g/ml-102 counts/sec.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A composition comprising a 10,10'-substituted-9,9'-biacridine conjugated to an antigen, a macromolecule, a protein, a nucleic acid, a hapten or a hapten conjugated to an antigen, a macromolecule, a protein, a nucleic acid or a hapten wherein at least one of the groups substituted at the 10 or 10' position of said biacridine is covalently bound to said antigen, protein, nucleic acid, macromolecule, hapten conjugate or hapten and a group substituted at the 10 and 10' position of the biacridine consists of a group disubstituted on the biacridine.

2. The composition of claim 1 wherein said 10,10'-substituted-9,9'-biacridine is a 10,10'-para-toluic acid-9,9'-biacridine, a 10,10'-para toluo-9,9'-biacridine, a 10,10'-aceto-9,9'-biacridine or a 10,10'-acetic acid-9,9'-biacridine.

3. A composition comprising a 10,10'-para-toluic acid-9,9'-biacridine dinitrate bound to an antigen, a nucleic acid, a macromolecule, a protein, a hapten or a hapten conjugated to a nucleic acid, an antigen, a macromolecule, a protein or a hapten wherein at least one of the groups substituted at the 10 or 10' position of said biacridine dinitrate is covalently bound to the antigen, protein, macromolecule, hapten or the hapten conjugate.

4. A composition comprising a 10,10'-acetic acid-9,9'-biacridine dinitrate bound to an antigen, a nucleic acid, a macromolecule, a protein, a hapten or a hapten conjugated to a nucleic acid, an antigen, a macromolecule, a protein or a hapten wherein at least one of the groups substituted at the 10 or 10' position of said biacridine dinitrate is covalently bound to the antigen, protein, macromolecule, hapten or hapten conjugate.

5. A chemiluminescent system for emitting measurable light useful in a chemical assay, an immunoassay, a ligand binding assay or a nucleotide assay, said system comprising: at a pH ranging from about 10.0 to about 14.0, a 10,10'-substituted-9,9'-biacridine having an oxidation potential, a signal solution having an oxidant or a combination of oxidants capable of overcoming the oxidation potential of said 10,10'-substituted-9,9'-biacridine, said 10,10'-substituted-9,9'-biacridine being bound to an analyte, or to a specific binding partner of an analyte or to a ligand of a specific binding partner to an analyte wherein said biacridine is bound by covalent binding of at least one of the substituted groups at the 10 or 10' position of said biacridine and a group substituted at the 10 and 10' position of the biacridine consists of a group disubstituted on the biacridine.

6. The chemiluminescent system of claim 5 wherein the 10,10'-substituted-9,9'-biacridine is a 10,10'-para-toluic acid-9,9'-biacridine or a 10,10'-acetic acid-9,9'-biacridine.

7. The chemiluminescent system of claim 5 further comprising a buffer solution, a chelating agent, a sulfoxide, a reducing sugar, and an alcohol.

8. The chemiluminescent system of claim 7 having a combination of oxidants wherein the 10,10'-substituted-9,9'-biacridine is a 10,10'-para-toluic acid-9,9'-biacridine or a 10,10'-acetic acid-9,9'-biacridine, the buffer solution is aqueous sodium tetraborate, the chelating agent is ethylenediaminetetraacetic acid, the sulfoxide is dimethyl sulfoxide, the reducing sugar is D(-) fructose and the alcohol is 2-Methyl2-propanol.

9. The chemiluminescent system of claim 5 wherein said analyte is a nucleic acid, an antigen, a hapten, a macromolecule, a protein or a hapten conjugated to an antigen, a macromolecule, a protein, a nucleic acid or a hapten.

10. The chemiluminescent system of claim 5 wherein said binding partner is a nucleotide probe, an antigen, a hapten, a macromolecule, a protein or a hapten conjugated to an antigen, a macromolecule, a protein, a nucleic acid or a hapten.

11. The chemiluminescent system of claim 5 wherein said ligand is an antigen, a hapten, a macromolecule, a protein or a hapten conjugated to a nucleic acid, an antigen, a macromolelcule, a protein or a hapten.

12. The chemiluminescent system of claim 6 wherein said 10,10'-substituted-9,9'-biacridine luminescent derivative is bound to the analyte, the specific binding partner of the analyte or to the ligand of a specific binding partner of the analyte by means of a biotin-avidin or biotin-streptavidin bridge.

13. A chemiluminescent system for emitting measurable light useful in a chemical assay, a ligand binding assay or a nucleic acid assay comprising: a 10,10'-substituted-9,9'-biacridine label bound to an analyte, or to a specific binding partner of an analyte or to a ligand of a specific binding partner to an analyte, and a signal solution which comprises at a pH ranging from about 10.0 to about 14.0 the oxidant potassium superoxide or a combination of oxidants comprising osmium tetroxide and potassium superoxide, wherein said biacridine label is bound by covalent binding of at least one of the substituted groups at said 10 or 10' position of said biacridine label and a roup substituted at the 10 and 10' position of the biacridine consists of a goup disubstituted on the biacridine.

14. The chemiluminescent system of claim 13 wherein said 10,10'-substituted-9,9'-biacridine label is 10,10'-paratoluic acid-9,9'-biacridinium dinitrate, 10,10'-para-toluo-9,9'-biacridinium dinitrate, a 10,10'-aceto-9,9'-biacridinium dinitrate or 10,10'-acetic acid-9,9'-biacridinium dinitrate.

15. The chemiluminescent system of claim 13 wherein said signal solution comprises the combination of oxidants and further comprises a buffer solution, a chelating agent, a sulfoxide, a reducing sugar, and an alcohol.

16. The chemiluminescent system of claim 15 wherein said buffer solution is aqueous sodium tetraborate, the chelating agent is ethylenediaminetetraacetic acid, the sulfoxide is dimethyl sulfoxide, the reducing sugar is D(-) fructose and the system further comprises the alcohol 2-Methyl-2-propanol.

17. The chemiluminescent system of claim 13 wherein said biacridine label is bound to the analyte, the specific binding partner of the analyte or to the ligand of a specific binding partner of the analyte by means of a biotin-avidin or biotin-streptavidin bridge.

18. A method for using a 10,10'-substituted-9,9'-biacridine in a chemiluminescent homogeneous assay for detecting the presence of or measuring the amount of an analyte in a sample comprising:
(a) providing a solid phase coated with a specific binding partner for said analyte;
(b) contacting said solid phase with said sample and with a predetermined amount of a 10,10'-substituted-9,9'-biacridine-analyte conjugate, said 10,10'-substituted-9,9'-biacridine having an oxidation potential, and with a predetermined amount of a polyanion that prevents unbound 10,10'-substituted-9,9'-biacridine-analyte conjugate from mediating luminescence, at least some of said specific binding partner binding to at least some of said 10,10'-substituted-9,9'-biacridine-analyte conjugate wherein said 10,10'-substituted-9,9'-biacridine is bound by covalent binding of at least one of said substituted groups at said 10 or 10' position of said 10,10'-substituted-9,9'-biacridine and a group substituted at the 10 and 10' position of the biacridine consists of a group disubstituted on the biacridine;
(c) contacting the solid phase from (b) with a signal solution comprising at a pH ranging from about 10.0 to about 14.0, an oxidant that overcomes or a combination of oxidants that overcome the oxidation potential of the 10,10'-substituted-9,9'-biacridine in the bound 10,10'-substituted-9,9'-biacridine-analyte conjugate to emit light; and (d) measuring the amount of light emitted in (c) wherein said amount of emitted light will be indirectly proportional to the amount of analyte present in said sample.

19. The method of claim 18 wherein said 10,10'-substituted-9,9'-biacridine is a 10,10'-para-toluic acid-9,9'-biacridine derivative or a 10,10'-acetic acid-9,9'-biacridine derivative.

20. The method of claim 18 wherein the signal solution further comprises an aqueous buffer solution, a chelating agent, a sulfoxide, a reducing sugar and an alcohol.

21. The method of claim 18 wherein said signal solution comprises the oxidants osmium tetroxide and potassium superoxide and further comprises aqueous sodium tetraborate, ethylenediaminetetraacetic acid, dimethyl sulfoxide, D(-) fructose and 2-Methyl-2-propanol.

22. A method for using a 10,10'-substituted-9,9'-biacridine in a chemiluminescent heterogeneous assay for detecting the presence of a first and second analyte in a sample comprising:
(a) providing a solid phase coated with a first specific binding partner and a second specific binding partner, said first binding partner being specific for said first analyte and said second binding partner being specific for said second analyte;
(b) contacting said solid phase with said sample and with a luminescent label-first analyte conjugate and a 10,10'-substituted-9,9'-biacridine label-second analyte conjugate wherein said 10,10'-substituted-9,9'-biacridine label is bound by covalent binding of at least one of said substituted groups at said 10 or 10' position of said 10,10'-substituted-9,9'-biacridine, a group substituted at the 10 and 10' position of the biacridine consists of a group disubstituted on the biacridine and the luminescent label and the 10,10'-substituted-9,9'-biacridine are not the same molecule, at least some of said first analyte conjugate binding to at least some of said first binding partner and at least some of said second analyte conjugate binding to at least some of said second binding partner;
(c) separating unbound conjugates from bound conjugates by washing said contacted solid phase;
(d) contacting said washed solid phase in (c) with either a signal solution specific for said 10,10'-substituted-9,9'-biacridine label or a signal solution specific for said luminescent label to produce light by means of a chemical reaction;
(e) detecting or measuring said light from said reaction in (d);
(f) contacting the solid phase from (d) with a signal solution specific for said 10,10'-substituted-9,9'-biacridine label, if the signal solution in (d) was a solution specific for said luminescent label, or with a signal solution specific for said luminescent label, if the solution in (d) was a solution specific for said 10,10'-substituted-9,9'-biacridine label, to produce light by means of a chemical reaction;
(g) detecting or measuring said light from said reaction in (f); and
(h) detecting said first and said second analyte or determining the amount of said first or said second analyte from the light detected or measured in steps (e) and (g).

23. The method of claim 22 wherein said 10,10'-substituted-9,9'-biacridine label is a 10,10'-paratoluic acid-9,9'-biacridinium dinitrate, a 10,10'-para-toluo-9,9'-biacridinium dinitrate, a 10,10'-aceto-9,9'-biacridinium dinitrate or a 10,10'-acetic acid-9,9'-biacridinium dinitrate.

24. The method of claim 22 wherein the luminescent label is deuteroporphyrin IX●2HCl.

25. The method of claim 24 wherein the washed solid phase from (c) is contacted in step (f) with said signal solution specific for deuteroporphyrin IX●2HCl which comprises at a pH ranging from about 10.0 to about 14.0, trans, trans-5-(4-Nitrophenyl)-2,4-pentadienal, sodium di-2-ethylhexyl sulfosuccinate, luminol or isoluminol, glucose, benzyltrimethylammonium hydroxide, cumene hydroperoxide, trisodium para periodate, and ethylenediaminetetraacetic acid.

26. The method of claim 23 wherein the washed phase from (c) is contacted in step (f) with said signal solution specific for a 10,10'-substituted-9,9'-biacridine which comprises in a sodium tetraborate aqueous solution, ethylenediaminetetraacetic acid, dimethyl sulfoxide, D(-) fructose, potassium superoxide, and 2-Methyl-2propanol.

27. In a ligand binding assay method for determining the presence or measuring the concentration of an unknown amount of an analyte in a fluid sample wherein said sample is contacted with a specific binding partner of said analyte and a ligand of said specific binding partner, either said ligand or said specific binding partner being bound to a chemiluminescent label and wherein any complexes formed between said ligand or said specific binding partner and said analyte are determined by means of contacting said chemiluminescent label with a signal solution to produce light from said label, an improvement is set out comprising using a 10,10'-substituted-9,9'-biacridine as the label and a mixture of ethylenediaminetetraacetic acid, dimethyl sulfoxide, D(-) fructose, potassium superoxide and 2-Methyl-2-propanol in aqueous sodium tetraborate as the signal solution, and a group substituted at the 10 and 10' position of the biacridine consists of a group disubstituted on the biacridine.

28. In a method for detecting the presence or amount of an analyte in a sample via a chemiluminescent sandwich assay that utilizes a signal solution and a luminescent molecule wherein said sample is contacted with a first specific binding partner to said analyte, a first and second specific binding partner to said analyte, a first specific binding partner to said analyte and a ligand to said first specific binding partner or a first and second specific binding partner to said analyte and a ligand to either said first or second specific binding partner, either said first or second specific binding partner, said ligand to said first or second binding partner or said first or second binding partner to said analyte being bound to said luminescent molecule and wherein any complexes formed between either of said specific binding partners and said analyte or said ligand to said first or second binding partner and said analyte are detected by means of contacting said luminescent molecule with a signal solution to produce light from said luminescent molecule, an improvement which comprises:

utilizing as said luminescent molecule a 10,10'-substituted-9,9'-biacridine, wherein said 10,10'-substituted-9,9'-biacridine is bound to said analyte or to said first or second specific binding partner to said analyte or to said ligand of a binding partner of said analyte by covalent binding of at least one of said substituted groups at said 10 or 10' position of said 10,10'-substituted-9,9'-biacridine and a group substituted at the 10 and 10' position of the biacridine consists of a group disubstituted on the biacridine, utilizing a predetermined amount of polyanion that prevents the biacridine in an unbound biacridine-labeled compound from mediating luminescence, and utilizing as said signal solution a solution comprising at a pH from about 10.0 to about 14.0, ethylenediaminetetraacetic acid, dimethyl sulfoxide, D(-) fructose, potassium superoxide and 2-Methyl-2-propanol in an aqueous sodium tetraborate solution.

29. A chemiluminescent system for producing measurable light by means of at least two different kinds of molecules and useful in a chemical assay, ligand binding assay, immunoassay or nucleotide assay for detecting more than one analyte in a sample comprising at a pH ranging from about 10.0 to about 14.0, deuteroporphyrin IX●2HCl coupled to a first analyte or to a specific binding partner of said first analyte or to a ligand of a specific binding partner of said first analyte, a 10,10'-substituted-9,9'-biacridine luminescent label bound to a second analyte or to a specific binding partner of said second analyte or to a ligand of a specific binding partner of said second analyte, said biacridine luminescent label being covalently bound by at least one of the substituted groups at the 10 or 10' position of said substituted biacridine and a group substituted at the 10 and 10' position of the biacridine consists of a group disubstituted on the biacridine, a first signal solution comprising a mixture of trans,trans-5-(4-nitrophenyl)-2,4-pentadienal, sodium di-2-ethylhexyl sulfosuccinate, luminol, glucose, benzyltrimethylammonium hydroxide, cumene hydroperoxide, trisodium para periodate, potassium superoxide and ethylenediaminetetraacetic acid and a second signal solution comprising a mixture of EDTA, DMSO, D(-) fructose, $KO_2$ and 2-Methyl-2-propanol in aqueous sodium tetraborate.

30. The luminescent system of claim 29 further comprising a predetermined amount of a polycation.

31. The luminescent system of claim 29 further comprising a predetermined amount of a polyanion.

* * * * *